(12) United States Patent
Adams et al.

(10) Patent No.: US 7,785,337 B2
(45) Date of Patent: Aug. 31, 2010

(54) SURGICAL MICRO-BURRING INSTRUMENT AND METHOD OF PERFORMING SINUS SURGERY

(75) Inventors: Kenneth M. Adams, Jacksonville, FL (US); Cecil O. Lewis, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1600 days.

(21) Appl. No.: 10/657,915

(22) Filed: Sep. 9, 2003

(65) Prior Publication Data

US 2005/0054972 A1 Mar. 10, 2005

(51) Int. Cl.
*A61B 17/32* (2006.01)
(52) U.S. Cl. ........................................ 606/180; 604/22
(58) Field of Classification Search ............. 606/79–80, 606/85, 167, 170, 180, 159; 604/22
See application file for complete search history.

(56) References Cited

U.S. PATENT DOCUMENTS

| | | | | |
|---|---|---|---|---|
| 3,844,272 A | | 10/1974 | Banko | |
| 4,530,356 A | * | 7/1985 | Helfgott et al. | ............. 606/171 |
| 4,850,354 A | * | 7/1989 | McGurk-Burleson et al. | .... 606/170 |
| 5,320,635 A | * | 6/1994 | Smith | ......................... 606/180 |
| 5,364,395 A | * | 11/1994 | West, Jr. | ...................... 606/46 |
| 5,741,287 A | * | 4/1998 | Alden et al. | ................. 606/170 |
| 5,913,867 A | * | 6/1999 | Dion | ........................... 606/180 |
| 5,922,003 A | * | 7/1999 | Anctil et al. | ................. 606/170 |
| 5,957,945 A | * | 9/1999 | Bays | ........................... 606/180 |
| 5,964,777 A | * | 10/1999 | Drucker | ....................... 606/180 |
| 6,001,116 A | * | 12/1999 | Heisler et al. | ................ 606/180 |
| 6,068,641 A | * | 5/2000 | Varsseveld | ................... 606/170 |
| 6,214,009 B1 | | 4/2001 | Toriumi et al. | |
| 6,280,447 B1 | * | 8/2001 | Marino et al. | .................. 606/88 |
| 6,293,957 B1 | | 9/2001 | Peters et al. | |
| 6,312,438 B1 | * | 11/2001 | Adams | ........................ 606/159 |
| 6,503,263 B2 | | 1/2003 | Adams | |
| 6,902,559 B2 | * | 6/2005 | Taufig | ......................... 604/542 |
| 6,916,328 B2 | * | 7/2005 | Brett | ........................... 606/167 |

OTHER PUBLICATIONS

PCT Search Report mailed Dec. 29, 2004 (7 pgs).

\* cited by examiner

*Primary Examiner*—Eduardo C Robert
*Assistant Examiner*—Mary Hoffman
(74) *Attorney, Agent, or Firm*—Dicke, Billig & Czaja, PLLC

(57) ABSTRACT

A surgical micro-burring instrument including an outer tubular member coaxially maintaining an inner tubular member. The outer tubular member defines a proximal section, a distal section, and a central lumen extending from the proximal section to the distal section. The distal section forms a pocket and an elevator tip. The pocket has a bottom wall and an opposed upper opening. The elevator tip extends distal the pocket. The inner tubular member forms a bur received within the pocket. Upon final assembly, at least a portion of the bur is exposed relative to the outer tubular member via the upper opening of the pocket. The elevator tip is configured to facilitate lifting of soft tissue, such as mucosa, while positioning the bur, via the pocket, in an appropriate location for cutting contacted harder tissue, such as turbinate bone or septal bone/cartilage.

29 Claims, 7 Drawing Sheets

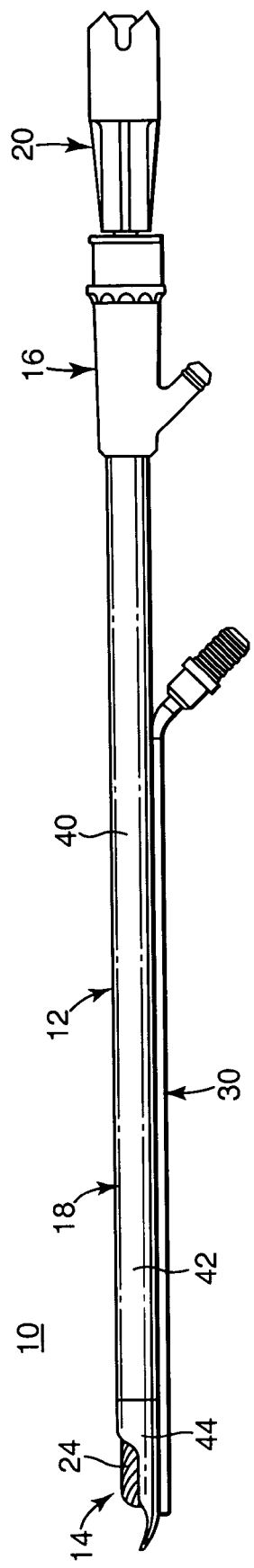
Fig. 1
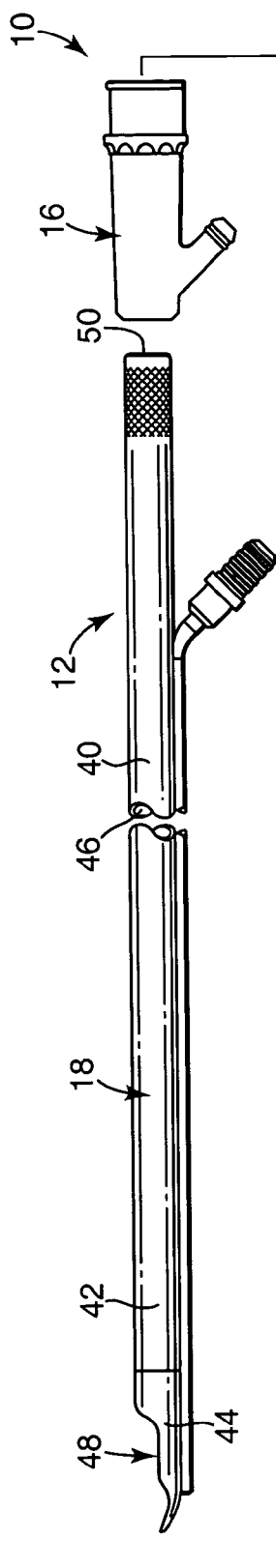
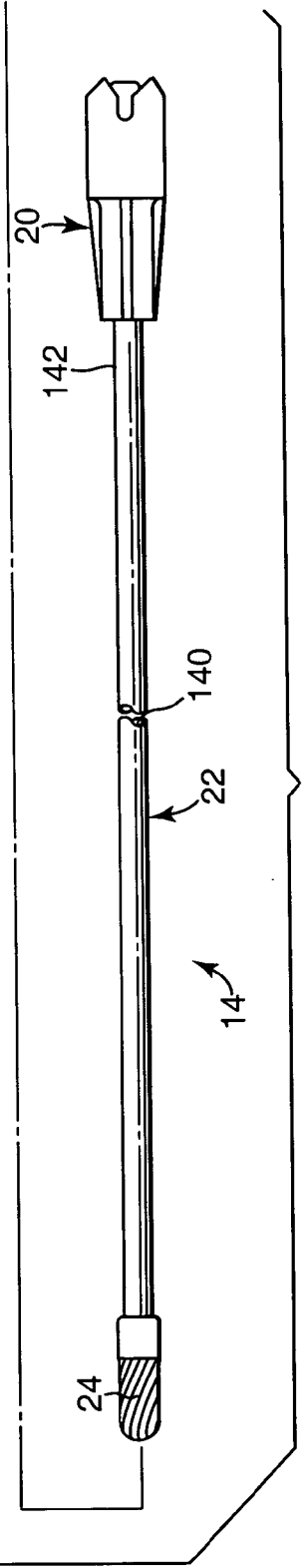
Fig. 2

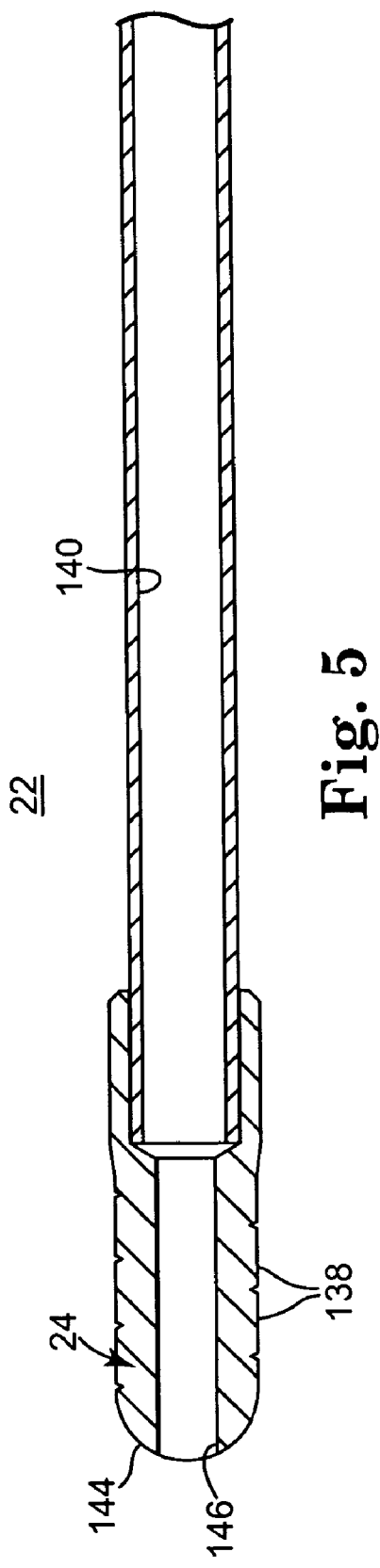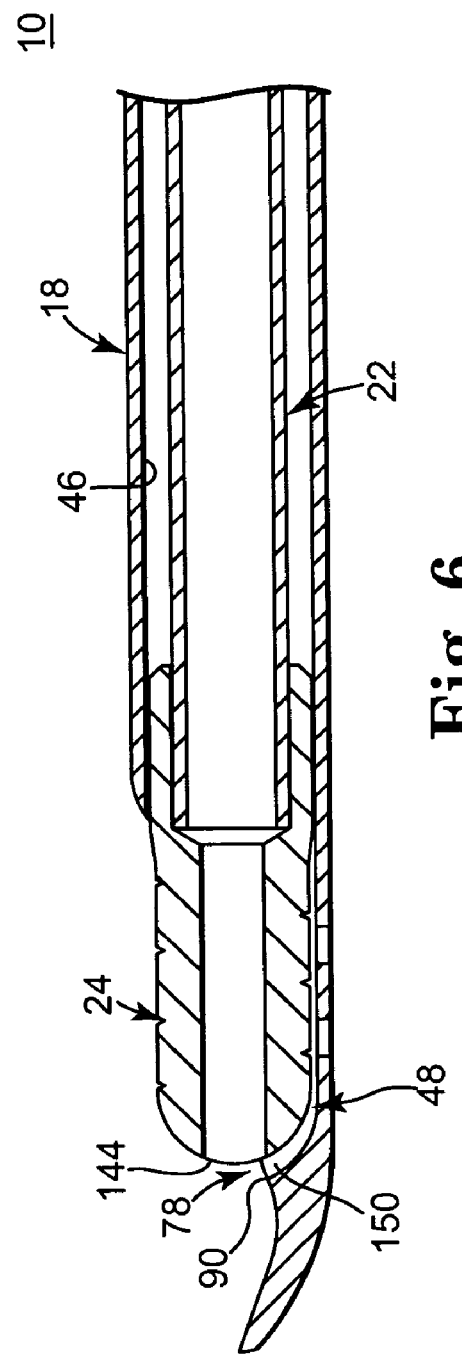

SURGICAL MICRO-BURRING INSTRUMENT AND METHOD OF PERFORMING SINUS SURGERY

BACKGROUND

The present invention relates to a surgical burring instrument. More particularly, it relates to a surgical micro-burring instrument the distal tip of which is configured to assist in tissue separation as part of a surgical procedure and is particularly useful for septoplasty and turbinoplasty procedures.

Numerous procedures have been developed to correct or address sinus abnormalities. One such procedure, known as a septoplasty, is performed to correct a deformity of the nasal septum. The nasal septum is generally comprised of cartilage (septal cartilage) in the front and thin bone in the back, lined with a thin membrane of tissue known as mucosa. The nasal septum is normally straight. Over time, however, there is a tendency for the septum to bend to one side or the other, or for an irregular shelf of cartilage or bone to develop, resulting in a deviated septum. The septoplasty procedure is performed to correct this deformity of the nasal septum. In general terms, a small incision is made inside the nose the mucosal lining of the septum is lifted or detached from the cartilage and bone. The deviated portions of the septum are removed or straightened (such as be resecting or debriding the deviated cartilage and/or bone), and the nasal lining mucous membrane is replaced. Splits or packs are then placed in the nose to maintain the septum cartilage and bone in a preferred midline position. Currently, multiple manual instruments, such as cottle elevators, chisels, and osteotomes, are required to complete a septoplasty procedure. While well accepted, use of these manual instruments require elevation of mucosal flaps on both sides of the septum to prevent mucosal tearing when removing bone and/or cartilage, provide only limited access to deviations of the maxillary crest, and can be quite time consuming. Notably, similar concerns arise with other sinus surgeries, such as submucosal removal of turbinate bone (e.g., turbinoplasty).

Powered surgical instruments have been developed for use in other, unrelated ear-nose-throat (ENT) operations. For example, U.S. Pat. No. 6,214,009, the teachings of which are incorporated herein by reference, describes a powered rhinoplasty bur instrument including an inner bur assembly rotatably received within an outer tubular member. In one embodiment, the outer tubular member forms curved wings or flaps that extend laterally outwardly from a window or pocket through which the bur is exposed. The wings or flaps are specifically provided to facilitate the rhinoplasty procedure. Relative to the septoplasty operation, however, the wings or flaps are highly undesirable. In addition, a separate cottle elevator (or similar elevator device) would be required to perform a septoplasty procedure using the described rhinoplasty bur instrument.

Conversely, U.S. Pat. No. 6,503,263 describes a powered micro-resecting instrument in which an inner tubular member, having a toothed cutting tip at a distal end thereof, is co-axially maintained, in a reciprocally moveable fashion, within an outer tubular member. The outer tubular member forms a window or pocket through which the cutting tip is exposed, along with an elevator tip extending distally therefrom. While highly proficient for performing an inferior turbinate reduction procedure in which only soft tissue is to be removed, this micro-resecting instrument is ill-suited for hard bone or cartilage removal applications, such as is otherwise required with a septoplasty procedure, submucosal removal of turbinate bone, etc. Further, the contour of the described elevator tip may not meet the spacing needs associated with, for example, a septoplasty procedure.

Septal reconstruction with a surgical, micro-burring or micro-debriding instrument appears highly viable, and may eliminate the complications otherwise associated with accepted techniques requiring multiple, manual instruments. Unfortunately, currently available micro-burring instruments are not designed to satisfy the needs of the septal site. Therefore, a need exists for a surgical sinus micro-burring instrument particularly capable of facilitating a septoplasty procedure.

SUMMARY

One aspect of the present invention relates to a surgical micro-burring instrument including an outer tubular member coaxially maintaining an inner tubular member. The outer tubular member defines a proximal section, an intermediate section, a distal section, and a central lumen extending from the proximal section to the distal section. Further, the distal section forms a pocket and an elevator tip. The pocket is fluidly connected to the central lumen and has a bottom surface and an opposed upper opening. The elevator tip extends distal the pocket. The inner tubular member is rotatably received within the central lumen, with a distal end thereof forming a bur that is otherwise received within the pocket. Upon final assembly, at least a portion of the bur is exposed relative to the outer tubular member via the upper opening of the pocket. In one preferred embodiment, an irrigation tube is provided that fluidly connects one or more openings in the bottom surface of the pocket with an irrigation source. Regardless, the elevator tip is configured to facilitate lifting of soft tissue, such as the nasal lining mucous membrane, while positioning the bur, via the pocket, in an appropriate location for cutting or burring contacted tissue. In one embodiment, a position of the elevator tip relative to the bur is fixed upon final assembly; in another embodiment, the elevator tip is axially moveable relative to the bur.

Another aspect of the present invention relates to a method of performing a micro-burring procedure at a surgical target site. The method includes providing a surgical micro-burring instrument including an outer tubular member and an inner tubular member. The outer tubular member includes a distal section and a central lumen. The distal section forms a pocket and an elevator tip. The pocket is fluidly connected to the central lumen and forms an upper opening opposite a bottom surface thereof. The elevator tip extends distal the pocket. The inner tubular member is rotatably received within the central lumen, with a distal end thereof forming a bur that is otherwise received within, and at least partially exposed relative to, the pocket. A distal end of the instrument is positioned at the operative site. The elevator tip is maneuvered to separate soft tissue from harder tissue at the target site. The distal end of the instrument is positioned such that the exposed portion of the bur contacts the harder tissue at the target site. The bur is rotated to remove portions of the contacted harder tissue. Finally, the elevator tip is removed from the target site. In one preferred embodiment, the method is a septoplasty procedure such that the soft tissue is septal mucosa and the harder tissue includes at least one of septal cartilage and septal bone.

BRIEF DESCRIPTION OF THE DRAWINGS

FIG. 1 is a side view of a surgical micro-burring instrument in accordance with the present invention;

FIG. 2 is a side, exploded view of the instrument of FIG. 1;

FIG. 5 is an enlarged cross-sectional view of an inner tubular member portion of the instrument of FIG. 1;

FIG. 6 is an enlarged, cross-sectional view of a distal region of the instrument of FIG. 1;

DETAILED DESCRIPTION

Figure 3A:
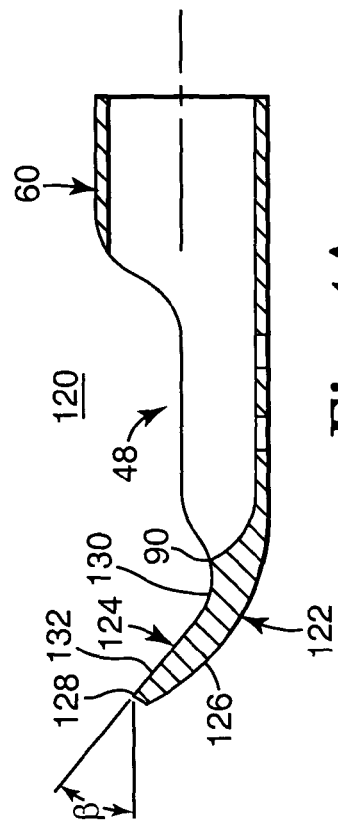
FIG. 3A is an enlarged, side view of a distal portion of an outer tubular member of the instrument of FIG. 1.

One preferred embodiment of a surgical micro-burring instrument 10 is illustrated in FIG. 1. The instrument 10 includes an outer tubular assembly 12 and an inner tubular assembly 14 (referenced generally in FIG. 1). The outer tubular assembly 12 includes an outer hub 16 and an outer tubular member 18, whereas the inner tubular assembly 14 includes an inner hub 20, and an inner tubular member 22 (illustrated in FIG. 2). The inner tubular member 22 is sized to be coaxially received within the outer tubular member 18 and forms a bur 24. As described in greater detail below, the micro-burring instrument 10 is configured to optimally perform a sinus surgical procedure, for example a septoplasty or turbinoplasty procedure.

The outer tubular member 18 extends distally from the outer hub 16. To this end, the outer hub 16 can assume a wide variety of forms known in the art. Additionally, and in one embodiment, an irrigation tube 30 is exteriorly secured to the outer tubular member 18. With this one configuration, a connector 32 is provided at one end of the irrigation tube 30, adapted to fluidly connect the irrigation tube 30 with an irrigation reservoir (not shown). An opposite end of the irrigation tube 30 is fluidly connected to a portion of the outer tubular member 18 as described in greater detail below. Alternatively, the outer tubular assembly 12 can be adapted to internally deliver irrigation fluid via the outer tubular member 18. Even further, the irrigation feature can be eliminated entirely.

With additional reference to FIG. 2, the outer tubular member 18 is an elongated tubular body defining a proximal section 40, an intermediate section 42, a distal section 44, and a central lumen 46. The central lumen 46 extends from the proximal section 40 to the distal section 44. In this regard, and as described in greater detail below, the distal section 44 forms a pocket or window 48 (referenced generally in FIG. 2) in fluid communication of the central lumen 46. Similarly, the proximal section 40 is open at a proximal end 50 thereof to facilitate positioning of the inner tubular member 22 within the central lumen 46.

The proximal section 40 is adapted to receive the outer hub 16, and thus has an appropriate outer diameter. The remainder of the outer tubular member 18, however, preferably provides a relatively uniform outer diameter selected to perform the desired sinus procedure and a relatively uniform inner diameter selected to rotatably receive the inner tubular member 22. For example, in one embodiment, the intermediate section 42, as well as the distal section 44 immediately proximal the pocket 48 has an inner diameter of approximately 3.5 mm that otherwise facilitates assembly and use of the inner tubular member 22/bur 24 as part of a septoplasty procedure. Alternatively, other dimensions can be employed.

Figure 3B:
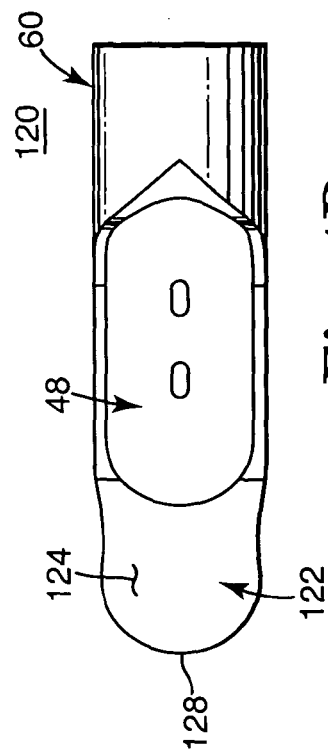
FIG. 3B is an enlarged, top view of FIG. 3A.

One preferred embodiment of the distal section 44 of the outer tubular member 18 is shown in greater detail in FIGS. 3A and 3B. As previously described, the distal section 44 forms the pocket 48 that is otherwise in fluid communication with the central lumen 46. In particular, the distal section 44 includes a proximal portion 60, the pocket 48, and an elevator tip 62. The proximal portion 60 is adapted to be contiguous with the intermediate section 42 (FIG. 2), providing a closed tubular section that continues the central lumen 46. As described in greater detail, the pocket 48 is formed distal the proximal portion 60, and the elevator tip 62 is formed distal the pocket 48.

The pocket 48 is defined by a side wall 70 (referenced generally in FIG. 3A) that forms a bottom surface 72, an end surface 74, and opposing side surfaces 76, and defines an upper opening 78 opposite the bottom surface 72. In one embodiment, one or more ports 80 are formed through the bottom surface 72 that otherwise fluidly connects the pocket 48 with the irrigation tube 30 (FIG. 1). As best shown by the cross-sectional view of FIG. 3A, the side surfaces 76 (one of which is shown in FIG. 3A) terminate in an edge 82 that otherwise defines a perimeter of the upper opening 78. In this regard, the edge 82 includes a proximal zone 84, an intermediate zone 86, and a distal zone 88. The proximal zone 84 extends downwardly (relative to the orientation of FIG. 3A) in a primarily angular fashion from the proximal portion 60. In one embodiment, this angular extension forms an included angle α in the range of 100°-140°, most preferably 120°, relative to a central axis A of the central lumen 46. The intermediate zone 86 extends in a primarily linear fashion (i.e., parallel with the central axis A) from the proximal zone 84. In one embodiment, relative to the longitudinal cross-sectional view of FIG. 3A, the intermediate zone 86 is aligned with the central axis A. In either case, the included angle α described above is thus also defined between the proximal and intermediate zones 84, 86 in longitudinal cross-section. Finally, the distal zone 88 extends downwardly (relative to the orientation of FIG. 3A) from the intermediate zone 86. In one embodiment, the distal zone 88 of the edge 82 defines a curve in longitudinal cross-section, with this curve being continued by the elevator tip 62. Regardless, the preferred pocket 48 provides a relatively large upper opening 78 so as to expose a relatively large portion of the bur 24 (FIG. 2) upon final assembly. Alternatively, other dimensions and/or configurations of the pocket 48 can also be employed.

The elevator tip 62 extends distally from the pocket 48, and in particular a distal-most end 90 thereof. In this regard, the elevator tip 62 includes an upper surface 100 and a lower surface 102 that combine to define a distal end point 104. The top surface 100 is generally defined by a proximal region 106 and a distal region 108. The proximal region 106 extends from the distal zone 88 of the pocket edge 82, preferably curving slightly upwardly (relative to the orientation of FIG. 3A) approximately commensurate with the curvature defined by the distal zone 88. The distal region 108 extends upwardly (relative to an orientation of FIG. 3A) from the proximal region 106 in a generally linear fashion (in longitudinal cross-section). In this regard, upward extension of the distal region 108 defines an included angle β in the range of 10°-50° relative to the central axis A of the lumen 46. With the one embodiment of FIGS. 3A-3B, the included angle β is approximately 20°, dictating that the distal end point 104 is positioned at or slightly below (relative to the orientation of FIG. 3A) the central axis A, as well as the intermediate zone 86 of the pocket edge 82. The lower surface 102 is preferably curved, generally conforming with the angular extension of the distal region 108 of the upper surface 100. With this one embodiment, the elevator tip 62 has a distal extension (i.e., longitudinal distance between the distal most end point 90 of the pocket 48 and the distal end point 104 of the elevator tip 62 of at least 0.05 inch (1.27 mm); more preferably at least 0.1 inch (2.54 mm); even more preferably at least 0.139 inch (3.53 mm) such that the distal end point 104 of the elevator tip 64 is discernably spaced from the pocket 48.

Figure 4A:
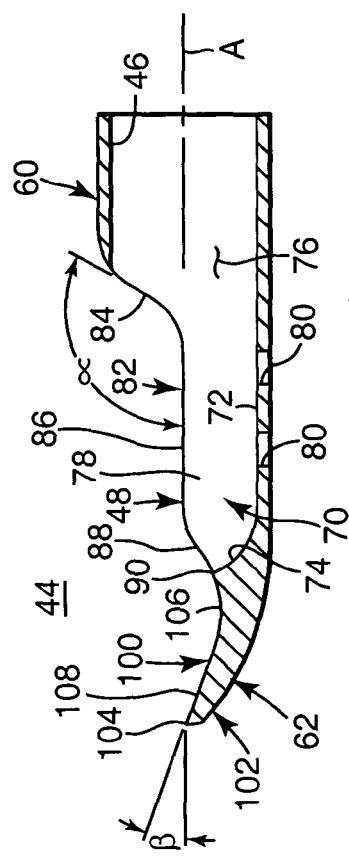
FIG. 4A is an enlarged, cross-sectional view of a distal portion of an alternative embodiment outer tubular member in accordance with the present invention.
Figure 4B:
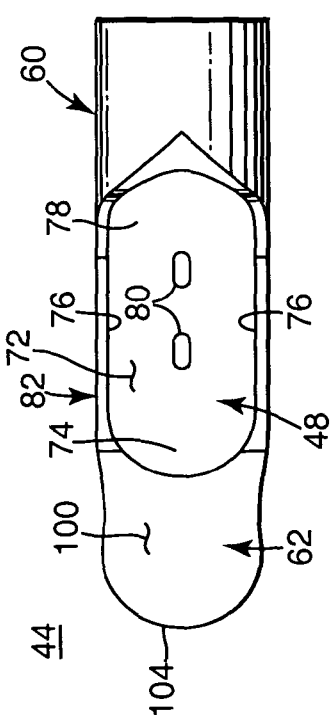
FIG. 4B is a top view of FIG. 4A.

Various features/dimensions of the above-described distal section 44 can be altered and remain within the scope of the present invention. For example, FIGS. 4A and 4B illustrate an alternative embodiment distal section 120 (otherwise provided as part of a tubular member akin to the outer tubular member 18 shown in FIG. 2). The distal section 120 is similar to the distal section 44 (FIGS. 3A and 3B previously described), and includes the proximal portion 60, the pocket 48, and an elevator tip 122. The proximal portion 60 and the pocket 48 are, in one embodiment, identical to the description provided above. Further, the elevator tip 122 again includes an upper surface 124 and a lower surface 126 that connect at a distal end point 128. The upper surface 124 includes a proximal region 130 and a distal region 132. The proximal region 130 defines an upward curvature commensurate with the curvature of the distal zone 88 of the pocket edge 82. As compared to the distal region 108 (FIG. 3A), the distal region 132 has a smaller radius of a curvature (in longitudinal cross-section). The distal region 132 extends in a generally upward fashion (relative to the orientation of FIG. 4A) from the proximal region 130, and is preferably generally linear in longitudinal cross-section. To this end, extension of the distal region 132 defines an included angle β of approximately 40° relative to the central axis A of the lumen 46, with the distal end point 128 being positioned above (relative to the orientation of FIG. 4A) the central axis A and the intermediate zone 86 of the pocket edge 82. Once again, however, the distal end point 128 is positioned at least 0.1 inch from the distal most end point 90 of the pocket 48.

Regardless of exact form, in one embodiment, the distal section 44 (FIG. 3A) or 120 (FIG. 4A) is formed separate from a remainder of the outer tubular member 18 (FIG. 2) and subsequently is assembled thereto. With this fabrication technique, the distal section 44, 120 can be formed from a material more amenable to precise manufacturing tolerances. For example, in one embodiment, the distal section 44, 120 is formed from heat-treated, 17-4 stainless steel, whereas a remainder of the outer tubular member is a 304 stainless steel material. Regardless, the so-formed distal section 44, 120 is secured to the intermediate section 42 of the outer tubular member 18, such as by a laser weld.

Returning to FIG. 2, and with additional reference to FIG. 5, the inner tubular member 22 extends from the inner hub 20. In one preferred embodiment, the inner hub 20 is configured for selective attachment to a handpiece (described in greater detail below) that can be operated to automatically rotate the inner tubular member 22 during use.

As previously described, the inner tubular member 22 forms the bur 24 at a distal end thereof. The bur 24 can assume a variety of forms and is adapted to cut or abrade bodily tissue upon rotation thereof. Thus, the bur 24 forms a plurality of cutting flutes 138. While a cylindrical bur configuration is shown, it will be appreciated that other configurations can be used including, but not limited to, spherical, hemispherical, ellipsoidal, and pear-shaped configurations.

In one embodiment, the inner tubular member 22 defines a central lumen 140 that extends from a proximal end 142 thereof. As best shown in FIG. 5, a distal end 144 of the bur 24 forms a hole 146 that is otherwise open to the central lumen 140. Alternatively, an exteriorly extending passage can be formed proximal the bur 24 that is otherwise fluidly connected to the central lumen 140. Regardless, the central lumen 140 serves as an aspiration conduit for the micro-burring instrument 10 (FIG. 1) as described below.

With reference to FIGS. 1 and 2, the micro-burring instrument 10 is assembled by coaxially positioning the inner tubular member 22 within the outer tubular member 18 via the central lumen 46. The inner hub 20 abuts against the outer hub 16. To this end, a position of the inner hub 20 relative to the bur 24 and a position of the outer hub 16 relative to the pocket 48 dictates a desired position of the bur 24 within the pocket 48 as best shown in FIG. 6. In particular, the inner tubular member 22 is coaxially disposed within the outer tubular member 18 such that the bur 24 is within the pocket 48 and exposed relative to the outer tubular member 18 via the upper opening 78 provided by the pocket 48. In one embodiment, a gap 150 is defined between the distal end 144 of the bur 24 and the distal end surface 74, and in particular the distal-most end point 90, of the pocket 48. The gap 150 is preferably provided to not only ensure free rotation of the bur 24 within the pocket 48, but also to provide sufficient space for delivery of irrigation fluid (such as the irrigation tube 30) and/or tissue removal via the aspiration lumen 140 otherwise provided by the inner tubular member 22. In one preferred embodiment, the gap 150 has a longitudinal dimension in the range of 0.0145-0.0255 inch (0.368-0.648 mm), more preferably 0.020 inch (0.508 mm). Alternatively, the bur 24 can be more closely positioned to the distal end of the surface 74 of the pocket 48.

Figure 7:
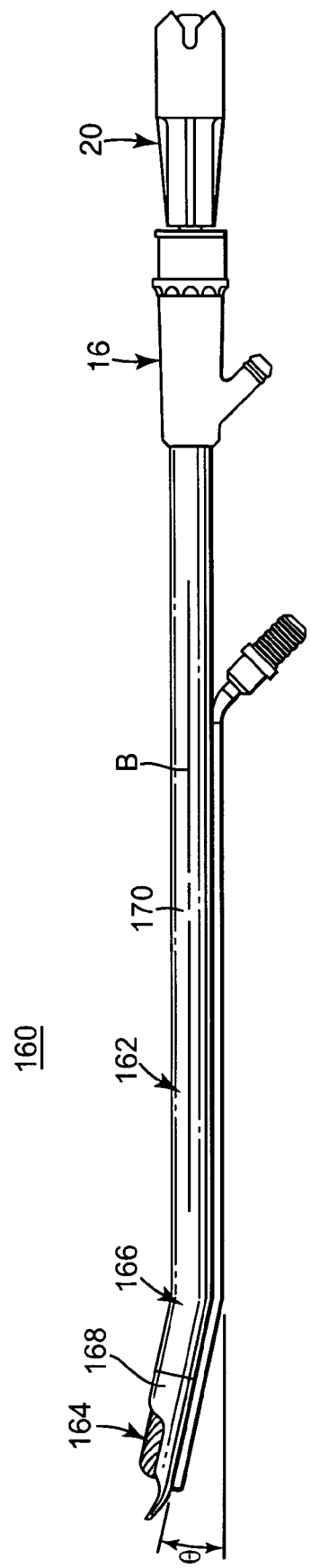
FIG. 7 is a side view of an alternative embodiment micro-burring instrument in accordance with the present invention.

While the micro-burring instrument 10 of the present invention has been illustrated as being relatively straight (e.g., relative to the view of FIG. 1, the outer tubular member 18 is relatively straight), other configurations can be employed than otherwise facilitate a desired procedure. For example, FIG. 7 illustrates an alternative embodiment micro-burring instrument 160 highly useful for a septoplasty procedure that again includes an outer tubular assembly 162 and an inner tubular assembly 164. The outer and inner tubular assemblies 162, 164 are, in one embodiment, highly similar to the outer and inner tubular assemblies 12, 14 (FIG. 1), respectively, previously described. However, with the alternative embodiment instrument 160 of FIG. 7, the outer and inner tubular members 162, 164 define a slight bend (referenced generally at 166) proximal a distal end portion 168 of the instrument 160. In one embodiment, the bend 166 defines an angle θ in the range of 10°-14°, more preferably approximately 12°, relative to a central axis B of a proximal portion 170 of the instrument 160. This bend 166 is particularly useful in properly positioning the distal end portion 68 during a septoplasty procedure. To facilitate necessary rotation of the inner tubular assembly 164 in the region of the bend 166 (such as for rotating the bur (unnumbered) at a distal end thereof), an inner tubular member (hidden in the view of FIG. 7, but akin to the inner tubular member 22 of FIG. 2)) is preferably flexible, formed of an appropriate material such as spiral wrap technology. Alternatively, other constructions can be employed.

Figure 8:
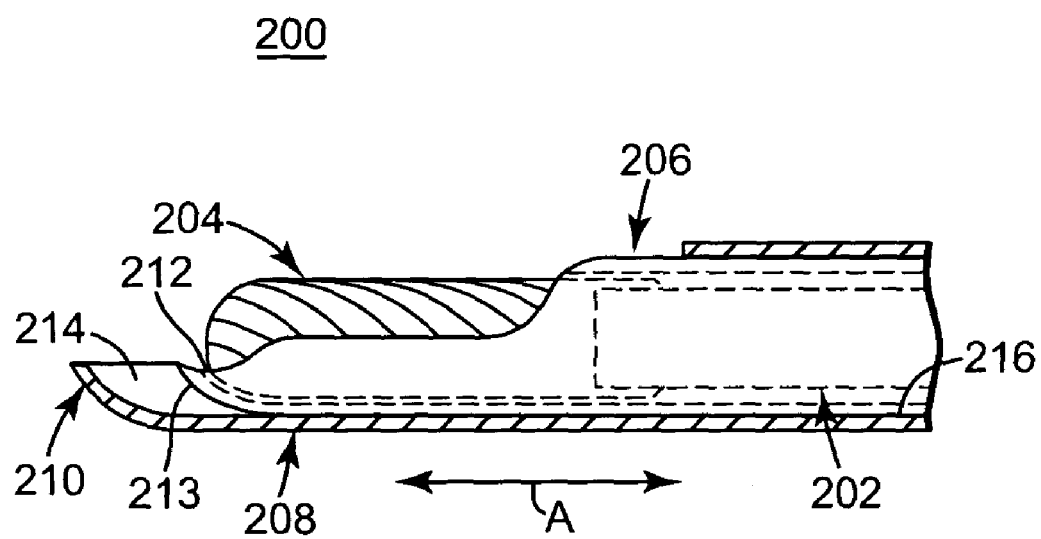
FIG. 8 is an enlarged, cross-sectional view of a distal portion of an alternative embodiment micro-burring instrument in accordance with the present invention.

While the micro-burring instrument of the present invention has been described as providing the elevator tip that is spatially fixed relative to the bur upon final assembly, other configurations are acceptable. For example, FIG. 8 depicts a distal portion of an alternative embodiment micro-burring instrument 200 in accordance with the present invention. The micro-burring instrument 200 includes an inner tubular member 202 having a bur 204 at a distal end thereof, an intermediate tubular member 206 and an outer tubular member 208. In general terms, the outer tubular member 208 forms an elevator tip 210, and is axially moveable along the intermediate tubular member 206 and thus is retractable relative to the bur 204 with respect to the position show in FIG. 8.

The inner tubular member 202 is preferably identical to the inner tubular member 22 (FIG. 2) previously described. Further, the intermediate tubular member 206 is preferably similar to the outer tubular member 18 (FIG. 2) previously described, except that the intermediate tubular member 206 does not form an elevator tip. Instead, the intermediate tubular member 206 defines a window 212, through which the bur 204 is exposed, terminating at a curved distal wall 213 that is otherwise not configured to facilitate lifting of tissue. In one embodiment, an irrigation tube (not shown, but akin to the irrigation tube 30 of FIG. 2) is structurally connected to an exterior of the intermediate tubular member 206 and fluidly connected to the window 212.

The outer tubular member 208 forms a pocket 214 proximal the elevator tip 210. In this regard, the elevator tip 210 can assume any of the forms previously described, as can the pocket 214. With the one embodiment of FIG. 8, the pocket 214 is open relative to a central lumen 216 otherwise defined by, and extending to a proximal section (not shown) of, the outer tubular member 208. The central lumen 216 is sized such that the outer tubular member 208 is co-axially received over the intermediate tubular member 206 in a slidable fashion. That is to say, the outer tubular member 208 is axially slidable along an outer diameter of the intermediate tubular member 206 in a direction shown by the arrow "A" in FIG. 8. Thus, the outer tubular member 208 serves as a sheath, and can be made from a variety of materials such as stainless steel, etc.

In one embodiment, the outer tubular member 208 forms a slot (not shown) that is received over the irrigation tube (not shown, but akin to the irrigation tube 30 of FIG. 2) otherwise affixed to the intermediate tubular member 206 to prevent the outer tubular member 208 from rotating relative to the intermediate tubular member 206. Further, a hub component (not shown) is preferably connected to a proximal end of the outer tubular member 208 and is configured to selectively lock the outer tubular member 208 to the intermediate tubular member 206 at desired axial positions.

Upon final assembly and during use, an axial position of the elevator tip 210 relative to the bur 204 can be altered by sliding the outer tubular member 208 along the intermediate tubular member 206. With this configuration, then, an exposed length of the elevator tip 210 can be selectively increased to effectuate a desired tissue lifting or separating procedure. Subsequently, the elevator tip 210 can be axially retracted relative to the bur 204 and with some configurations, entirely removed from a region of the bur 204.

Figure 9A:
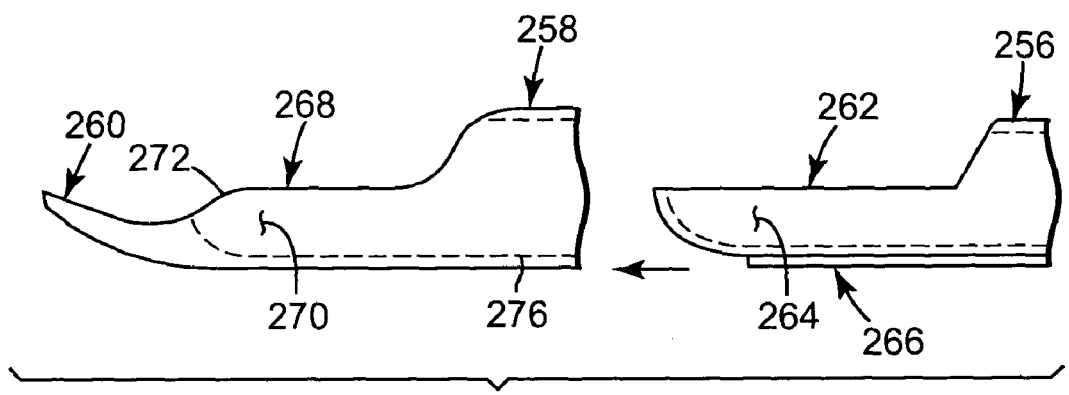
FIG. 9A is an enlarged, exploded view of a distal portion of an alternative embodiment micro-burring instrument in accordance with the present invention.
Figure 9B:
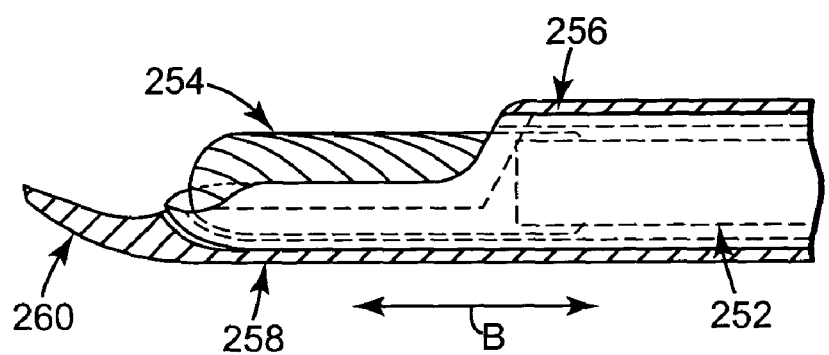
FIG. 9B is a cross-sectional view of a portion of the instrument of FIG. 9A.

A portion of yet another alternative embodiment micro-burring instrument 250 is shown in FIGS. 9A and 9B. Similar to the instrument 200 of FIG. 8, the micro-burring instrument 250 includes an inner tubular member 252 having a bur 254 at a distal end thereof, an intermediate tubular member 256 and an outer tubular member 258. Once again, the outer tubular member 258 forms an elevator tip 260, and is axially moveable along the intermediate tubular member 256 and thus is axially moveable relative to the bur 254.

The inner tubular member 252, including the bur 254, is preferably identical to previous embodiments. The intermediate tubular member 256 is also similar to the intermediate tubular member 206 (FIG. 8) previously described, forming a window 262 and characterized by the absence of an elevator tip. As compared to the embodiment of FIG. 8, the window 262 defines a larger opening in that a sidewall 264 thereof extends only slightly upwardly (relative to the orientation of FIG. 9A). Finally, in one embodiment, an irrigation tube 266 is affixed to an exterior of the intermediate tubular member 256 and is fluidly connected to the window 262.

The outer tubular member 258 forms a pocket 268 proximal the elevator tip 260. Once again, the elevator tip 260 can assume any of the forms previously described. The pocket 268, and in particular a sidewall 270 that otherwise terminates at an edge 272 to define the pocket 268, is preferably similar in size and shape to the pocket 48 (FIG. 3A) previously described, and is fluidly connected to a central lumen 274 formed by the outer tubular member 258. Further, the sidewall 270 forms a slot 276 opposite the edge 272 that is sized to receive the irrigation tube 266 upon final assembly. Regardless, the central lumen 274 is sized to be co-axially received over, and axially slidable relative to, the intermediate tubular member 256. Thus, upon final assembly, the elevator tip 260 is axially moveable relative to the bur 254 in a direction shown by arrow "B" in FIG. 9B, such that the outer tubular member 258 serves a sheath. With the one embodiment of FIGS. 9A and 9B, interaction between the irrigation tube 266 and the slot 276 prevents the outer tubular member 258 from rotating relative to intermediate tubular member 256. Alternatively, the slot 276 and/or the irrigation tube 266 can be eliminated or replaced with varying constructions.

Regardless of exact form, the micro-burring instrument 10, 160, 200, 250 of the present invention is useful in performing various sinus operations, and finds particular usefulness as part of a septoplasty procedure. By way of example, and with reference to the one embodiment of FIGS. 1 and 2, the assembled instrument 10 is deployed to the sinus target site. For example, with a septoplasty procedure, the elevator tip 62 is directed between the mucosal lining of the septum and the instrument 10 is then maneuvered to lift or elevate the mucosal lining from the septum cartilage and/or bone via the elevator tip 62. Where the instrument 10 is configured to allow axial movement of the elevator tip 62 relative to the bur 24 (such as with the instrument 200 of FIG. 8 or the instrument 250 of FIGS. 9A and 9B), the elevator tip 62 is axially extended relative to the bur 24 prior to lifting of the mucosal lining. Once sufficient elevation is achieved, the bur 24 is positioned against the targeted septum cartilage and/or bone. The inner tubular member 22 is then rotated relative to the outer tubular member 18, such that the bur 24 burs (e.g., cuts or abrades) the contacted cartilage and/or bone. Where the elevator tip 62 is axially moveable relative to the bur 24, the elevator tip 62 can be retracted prior to, during, or after rotation of the bur 24. Regardless, the pocket 48 and the bur 24, and thus the target site, are periodically or continuously flushed with an irrigation fluid via, for example, the irrigation tube 30 that is otherwise fluidly connected to the pocket 48. Further, the pocket 48, and thus the target site, is periodically or continuously aspirated via the central lumen 140 (FIG. 5) of the inner tubular member 22 to remove abraded tissue from the pocket 48 and the target site. Once a desired amount of cartilage and/or boney tissue has been removed, rotation of the bur 24 is stopped, and the instrument 10 removed from the target site, allowing the nasal lining mucous membrane to return to its natural position. If necessary, splints or packs are placed in the nasal cavity to ensure approximately mid-line positioning of the septum.

In addition to the septoplasty procedure described above, the micro-burring instrument 10, 160, 200, 250 of the present invention can be used to perform a variety of other sinus procedures. For example, submucosal removal of turbinate bone or septal bone/cartilage can be achieved with the instrument of the present invention, whereby only a relatively small puncture wound is required to provide sufficient access to the target site, in contrast to current techniques in which a relatively invasive incision is required to cut or resect turbinate bone (in addition to removal of other, softer tissue). In short, the micro-burring instrument of the present invention is useful for performing a wide variety of surgical procedures in which soft tissue is desirably lifted from harder tissue and then the harder tissue (or portions thereof) removed in a minimally invasive fashion. For example, sub-fascial and sub-perichrondrial removal of bony spurs in the spine are readily achieved in accordance with the present invention.

Figure 10:
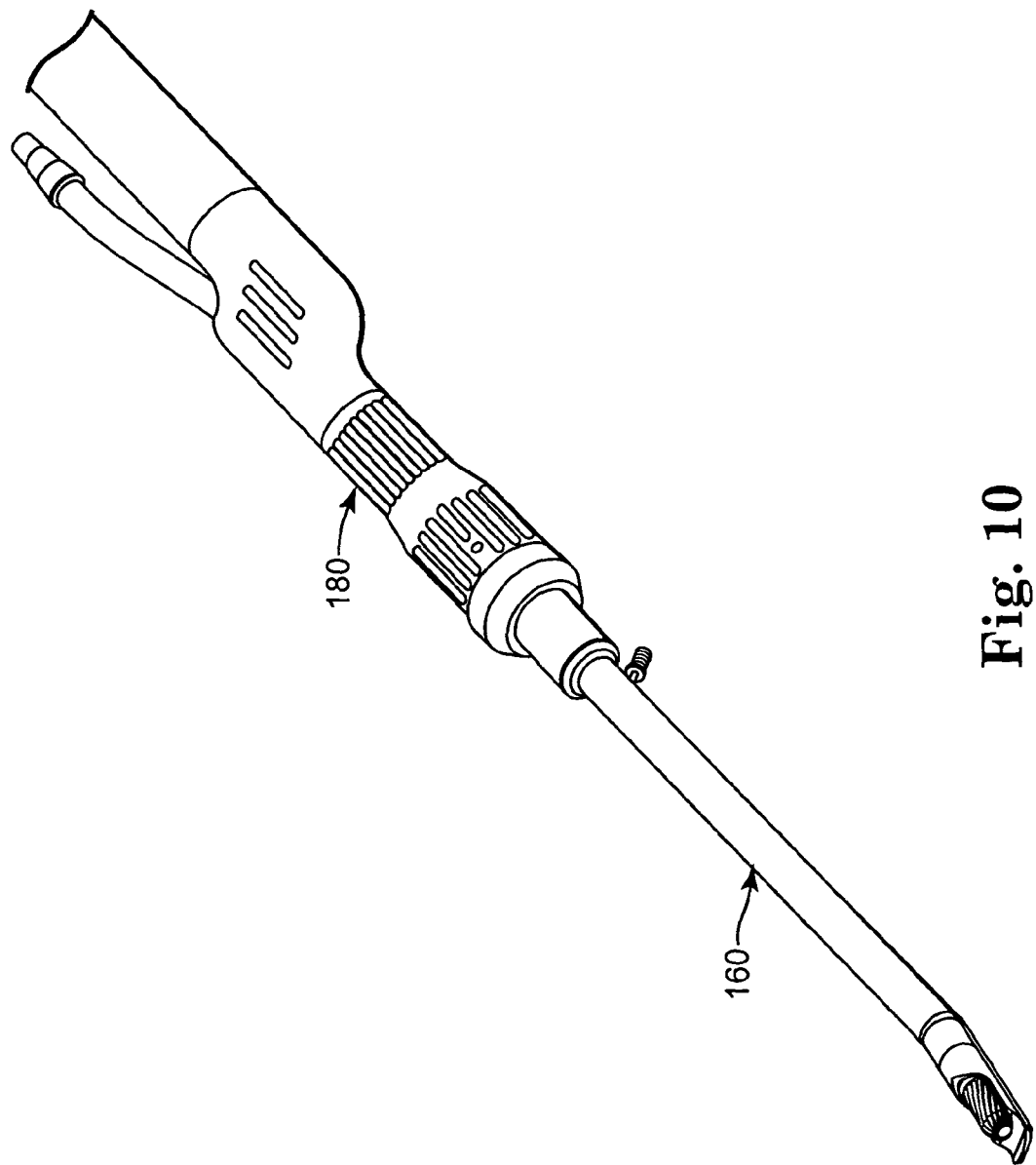
FIG. 10 is a perspective view of the instrument of FIG. 1 assembled to a powered handpiece.

Regardless, and in one embodiment, the micro-burring instrument 10, 160, is attached to a powered handpiece as shown in FIG. 10. The handpiece 280 can assume a variety of forms known in the art, and is in one preferred embodiment a StraightShot® powered handpiece, marketed by Medtronic-Xomed.

The surgical micro-burring instrument of the present invention provides a marked improvement over previous designs. With respect to sinus surgeries, for example septoplasty procedures, use of a micro-burring instrument provides a distinct advantage over currently-accepted techniques requiring multiple, manual tools. The elevator tip associated with the present invention readily facilitates lifting or elevation of soft tissue (such as the nasal lining mucous membrane) from harder tissue (such as septal cartilage and/or bone), and positions a rotatable bur at the target site endoscopically.

Although the present invention has been described with reference to preferred embodiments, workers skilled in the art will recognize that changes can be made in form and detail with departing from the spirit and scope of the present invention.

What is claimed is:

1. A surgical micro-burring instrument comprising:
   an outer tubular member having a proximal section, an intermediate section, a distal section, and a central lumen extending from the proximal section to the distal section, the distal section forming:
      a pocket fluidly connected to the central lumen, the pocket having a bottom surface and an opposed upper opening,
      an elevator tip extending distal the pocket,
      a proximal portion proximal the pocket, the proximal portion forming a tube,
      wherein the pocket is defined by a side wall having an upper edge including a proximal zone extending from the proximal portion, an intermediate zone extending from the proximal zone, and a distal zone extending from the intermediate zone to a distal-most end of the pocket at which the central lumen terminates,
      and further wherein relative to an orientation of the outer tubular member in which the bottom surface is the lowest-most surface of the pocket:
         the proximal zone extends downwardly from the proximal portion toward the bottom surface,
         the intermediate zone extends from the proximal zone at an angle of extension relative to the proximal zone that differs from an angle of extension of the proximal zone relative to the proximal portion,
         the distal zone extends downwardly from the intermediate zone toward the bottom surface at an angle of extension differing from the angle of extension of the intermediate zone relative to the proximal zone; and
   an inner tubular member rotatably received within the central lumen, a distal end of the inner tubular member forming a bur positioned within the pocket, such that upon final assembly, at least a portion of the bur is exposed relative to the outer tubular member via the upper opening of the pocket.

2. The instrument of claim 1, wherein the elevator tip distally extends at least 0.05 inch relative to the distal-most end of the pocket.

3. The instrument of claim 2, wherein the elevator tip includes an upper surface extending from the distal-most end of the pocket, the upper surface including a proximal region and a distal region, wherein at least a portion of the distal region extends from the proximal region in an angular fashion in longitudinal cross-section.

4. The instrument of claim 3, wherein the angular extension of the distal region defines an included angle in the range of 10°-50° relative to a central axis of the outer tubular member.

5. The instrument of claim 4, wherein the included angle is approximately 20°.

6. The instrument of claim 4, wherein the included angle is approximately 40°.

7. The instrument of claim 3, wherein at least a portion of the proximal region of the upper surface of the elevator tip extends downwardly from the distal-most end of the pocket.

8. The instrument of claim 7, wherein the proximal region is curved in longitudinal cross-section.

9. The instrument of claim 1, wherein the elevator tip terminates in a distal end point, and further wherein the distal end point is laterally above the distal-most end of the pocket when the outer tubular member is oriented such that the bottom surface of the pocket is below the upper opening.

10. The instrument of claim 1, wherein the proximal zone extends from the proximal portion in an angularly downward fashion.

11. The instrument of claim 10, wherein angular extension of the proximal zone defines an included angle in the range of 100°-140° relative to a central axis of the proximal portion.

12. The instrument of claim 11, wherein the included angle is approximately 120°.

13. The instrument of claim 1, wherein the intermediate zone is parallel with a central axis of the proximal portion.

14. The instrument of claim 1, wherein the bottom surface forms at least one opening fluidly connected to an irrigation source.

15. The instrument of claim 14, further comprising:
   an irrigation tube extending exteriorly along the outer tubular member and fluidly connected to the at least one opening.

16. The instrument of claim 1, wherein upon final assembly, a distal end of the bur is longitudinally spaced from the distal-most end point.

17. The instrument of claim 1, further comprising:
   an aspiration passage extending through the outer tubular member for aspirating cut tissue.

18. The instrument of claim 17, wherein the inner tubular member forms a lumen defining the aspiration passage with the bur forming an opening at a distal end thereof, and further wherein the opening is in fluid communication with the lumen of the inner tubular member.

19. The instrument of claim 1, wherein the intermediate section of the outer tubular member defines a longitudinal bend.

20. The instrument of claim 19, wherein the longitudinal bend is approximately 12° relative to a central axis defined by the proximal section.

21. The instrument of claim 1, wherein the instrument is adapted for use in a septoplasty procedure.

22. The instrument of claim 1, wherein the elevator tip is selectively axially moveable relative to the bur.

23. The instrument of claim 22, further comprising:
an intermediate tubular member co-axially disposed between the inner tubular member and the outer tubular member, the intermediate tubular member forming a distal window through which at least a portion of the bur is exposed;
wherein the outer tubular member is slidably received over the intermediate tubular member.

24. The instrument of claim 1, wherein the bur forms a plurality of cutting flutes.

25. The instrument of claim 1, wherein the bur has a shape selected from the group consisting of cylindrical, spherical, hemispherical, ellipsoidal, and pear.

26. The instrument of claim 1, wherein the distal-most end is below a central axis of the central lumen when the outer tubular member is spatially oriented such that the bottom surface is a lowest-most surface of the pocket.

27. The instrument of claim 1, wherein the bottom surface forms a plurality of ports opposite the upper opening.

28. The instrument of claim 18, wherein the distal end opening formed by the bur is in an axial opening, and further wherein the upper edge is shaped such that when the bur is in a distal-most position relative to the distal-most end of the pocket, the opening is unobstructed by the outer tubular member.

29. The instrument of claim 1, wherein the bur is configured to remove hard bone with rotation of the inner tubular member.

* * * * *